(12) United States Patent
Mathur et al.

(10) Patent No.: US 6,309,664 B1
(45) Date of Patent: Oct. 30, 2001

(54) METHODS, USES AND COMPOSITIONS OF FLUID PETROLATUM

(75) Inventors: Rajiv Mathur, Sewell; Nadya Lawrence, Cape May, both of NJ (US)

(73) Assignee: Igen, Incorporated, Wilmington, DE (US)

( * ) Notice: Subject to any disclaimer, the term of this patent is extended or adjusted under 35 U.S.C. 154(b) by 0 days.

(21) Appl. No.: 09/396,535

(22) Filed: Sep. 15, 1999

(51) Int. Cl.⁷ ................................................. A61K 9/127
(52) U.S. Cl. ........................... 424/450; 424/401; 424/43; 424/600; 424/617; 428/402.2; 514/847
(58) Field of Search .................... 424/450, 401, 424/43–47, 600, 617; 514/844, 847; 428/402.2

(56) References Cited

U.S. PATENT DOCUMENTS

| | | | |
|---|---|---|---|
| 127,568 | 6/1872 | Chesebrough . | |
| 4,895,452 | 1/1990 | Yiournas et al. | 366/173 |
| 4,911,928 | 3/1990 | Wallach | 424/450 |
| 5,160,669 | 11/1992 | Wallach et al. | 264/4.3 |
| 5,234,767 | 8/1993 | Wallach | 428/402.2 |
| 5,260,065 | 11/1993 | Mathur et al. | 424/450 |
| 5,405,615 | 4/1995 | Mathur | 424/450 |
| 5,439,967 | 8/1995 | Mathur | 424/450 |
| 5,561,062 | * 10/1996 | Varanelli | 435/238 |
| 5,643,600 | 7/1997 | Mathur | 424/450 |

OTHER PUBLICATIONS

Morrison, et al., "Petrolatum: A Useful Classic", *Cosmetics & Toiletries*, 111:59, 1996.

* cited by examiner

*Primary Examiner*—Gollamudi S. Kishore
(74) *Attorney, Agent, or Firm*—Lahive & Cockfield, LLP

(57) ABSTRACT

A fluid preparation of petrolatum capable of being sprayed on to a surface. The preparation includes paucilamellar lipid vesicles containing the petrolatum. Preferably, petrolatum comprises about 20–30% or more of the total weight of the vesicles. Methods of protecting the skin of mammals using the fluid preparation of petrolatum are also discussed.

16 Claims, No Drawings

METHODS, USES AND COMPOSITIONS OF FLUID PETROLATUM

BACKGROUND

Petrolatum and its manufacture were initially patented in 1872 by Robert A. Cheeseborough (U.S. Pat. Ser. No. 127,568). Although Cheeseborough cited treating leather as its primary use, petrolatum was also recommended as a hair pommenade and for treating chapped hands. In 1875, the American Pharmaceutical Association found petrolatum "without a superior" for treating burns and scalds. Since then, petrolatum's beneficial properties for skin care and treatment have been extensively studied and reported.

Petrolatum has been found to be the best material for relieving ordinary xerosis (Morrison et al., *Cos & Toil.* (1996) 111:59). Petrolatum's moisturizing characteristics have been ascribed to the slowed water loss when petrolatum is applied to the skin. Petrolatum has also been used extensively on wound dressings, both as a treatment and as a pharmaceutically acceptable ointment base to deliver other medicinal compositions.

However, the same hydrophobic properties which make petrolatum an effective moisture barrier, also make it difficult to evenly disperse in fluid aqueous preparations. When mixed with water, petrolatum immediately forms a separate distinct layer. Evenly dispersed fluid preparations are essential for commercial manufacturing techniques, such as spraying. This is true for petrolatum encapsulated in lipid vesicles as well as unencapsulated products.

Accordingly, it is an object of the present invention to provide methods and compositions relating to a sprayable petrolatum product consisting of lipid vesicles encapsulating petrolatum, dispersed in an aqueous phase.

Another object of this invention is to provide a stable dispersion of petrolatum containing lipid vesicles in water.

These and other objects and features of the invention will be apparent from the following descriptions.

SUMMARY OF THE INVENTION

The invention features a sprayable petrolatum product having lipid vesicles encapsulating petrolatum dispersed in an external aqueous phase. The vesicles comprise a primary wall forming material and a weighting agent. The primary wall forming material is selected from the group consisting of nonionic and zwiterionic surfactants and the weighting agent is present in an amount sufficient that the lipid vesicles have a density of about 0.95–1.0 g/ml. Examples of preferred weighting agents include, for example, high molecular weight polyoxyethylene sorbitan esters, ester gum, metal oxides (e.g., iron oxide), and combinations thereof. Advantageously, the primary wall forming material has the property that it will form a lipid vesicle in the absence of said weighting agent. Preferably, petrolatum comprises at least about 20%, and more preferably about 30%, by weight of the lipid vesicles.

The invention also pertains to a method for protecting the skin of a mammal by contacting the skin with a sprayable pharmaceutical petrolatum composition product. The sprayable pharmaceutical petrolatum composition product includes lipid vesicles encapsulating petrolatum dispersed in an external aqueous phase. These lipid vesicles comprise a primary wall forming material and a weighting agent. The primary wall forming material is a nonionic or a zwiterionic surfactant, and the weighting agent is present in an amount sufficient that the lipid vesicles have a density of about 0.95–1.0 g/ml. The preferred primary wall forming materials are polyoxyethylene glyceryl fatty acids, $C_{12}$–$C_{18}$ fatty alcohols, $C_{12}$–$C_{18}$ glycol monoesters, $C_{12}$–$C_{18}$ glyceryl mono- and diesters, polyoxyethylene fatty alcohols, betaines, sarcosinates, propylene glycerol stearate, sucrose distearate, glycerol dilaurate, glucosides, and mixtures thereof.

DETAILED DESCRIPTION OF THE INVENTION

The invention pertains to, at least in part, a sprayable petrolatum product having lipid vesicles encapsulating petrolatum dispersed in an external aqueous phase. The vesicles comprise a primary wall forming material and a weighting agent. The primary wall forming material is selected from the group consisting of nonionic and zwiterionic surfactants and the weighting agent is present in an amount sufficient that the lipid vesicles have a density of about 0.95–1.0 g/ml. Preferably, petrolatum comprises at least about 20%, e.g., more preferably 30%, by weight of the lipid vesicles. In a further embodiment, the lipid vesicles are paucilamellar.

Petrolatum has been commercially available since the mid-1870's. Commonly, it is a semisolid mixture of hydrocarbons and is, essentially, both odorless and tasteless to humans. Petrolatum is often obtained through the dewaxing of heavy mineral oils.

The primary wall forming material, which constitutes the greatest structural material by weight of the bilayers (e.g., 10–20%), can be any suitable non-ionic surfactant known in the art to be useful in forming vesicles. For example, suitable surfactants are disclosed in U.S. Pat. No. 5,260,065, entitled "Blended Lipid Vesicles;" U.S. Pat. No. 5,234,767, entitled "Lipid Hybrid Vesicles;" U.S. Pat. No. 5,439,967 entitled "Propylene Glycol Stearate Vesicles;" U.S. Pat. No. 5,405,615, entitled "Sucrose Distearate Vesicles," and U.S. Pat. No. 5,160,669, entitled "Method of Making Oil Filled Paucilamellar Lipid Vesicles," the contents all of which are incorporated by reference herein. Advantageously, the primary wall forming material has the property that it will form a lipid vesicle in the absence of said weighting agent. In another embodiment, the primary wall forming material of the vesicle bilayers is selected from the group consisting of polyoxyethylene glyceryl fatty acid esters (e.g., having 1–10 polyoxyethylene groups), such as polyoxyethylene glyceryl monostearate and polyoxyethylene glyceryl monooleate, $C_{12}$–$C_{18}$ fatty alcohols, $C_{12}$–$C_{18}$ glycol monoesters, $C_{12}$–$C_{18}$ glyceryl mono-and diesters, and mixtures thereof. Preferred primary wall forming material are selected from the group consisting of $C_{16}$ and $C_{18}$ fatty alcohols, glyceryl mono- and distearate, glyceryl dilaurate, glycol stearate, and mixtures thereof. All of the aforementioned compounds are commercially available. Preferred primary wall forming materials include $C_{16}$–$C_{18}$ fatty alcohols, glycol stearate, glyceryl mono- and distearate, glyceryl dilaurate, and combinations thereof.

The term "weighting agent" includes substances which affect the specific gravity of the lipid vesicles. Advantageously, the weighting agents increase the specific gravity of the vesicles to aid dispersion of the vesicles through out an aqueous mixture and to deter separation between the aqueous and lipid components of the mixture. Preferably, the inclusion of the weighting agents increases the specific gravity of the vesicles into the desired stable product range, e.g. greater than 0.95 g/mL to about 0.99 g/mL. In some embodiments of the invention, the weighting agents are incorporated directly into the walls of the vesicles. Preferred weighting agents include compounds with a specific gravity greater than 1.0 g/mL, (e.g., greater than 1.0 g/mL to about 2.0 g/mL). Examples include high molecular weight polyoxyethylene sorbitan esters, ester gums, metal oxides (e.g., iron oxide), and combinations thereof.

The lipid vesicles of the invention may further include one or more charge producing agents which minimize flow of the external aqueous phase into the vesicles. Preferred charge producing agents include negatively charged hydrophilic molecules such as sodium lauryl sulfate, sodium laureth sulfate, sodium lactate, sodium pyrrolidone carboxylate, aloe vera, retinoic acid and urea. Other possible negative charge producing agents include oleic acid, dicetyl phosphate, palmitic acid, cetyl sulphate, retinoic acid, phosphatidic acid, phosphatidyl serine, and mixtures thereof. Alternatively, also contemplated is the incorporation of positively charged molecules in order to provide a net positive charge to the vesicles. Examples of suitable positively charged molecules include, for example, long chain amines, e.g., stearyl amines or oleyl amines, long chain pyridinium compounds, e.g., cetyl pyridinium chloride, quaternary ammonium compounds, or mixtures of these can be used. A preferred positive charge producing material is hexadecyl trimethylammonium bromide, a potent disinfectant. The use of this disinfectant as the positive charge producing material within the vesicles provides a secondary advantage as the vesicles deteriorate; they act as a sustained release germicide carriers.

The vesicles may also include targeting molecules, either hydrophilic or amphiphilic, which can be used to direct the vesicles to a particular target in order to allow release of the material encapsulated in the vesicle at a specified biological location. If hydrophilic targeting molecules are used, they can be coupled directly or via a spacer to an OH residue of the polyoxyethylene portion of the surfactant, or they can be coupled, using state of the art procedures, to molecules such as palmitic acid, long chain amines, or phosphatidyl ethanolamine. If spacers are used, the targeting molecules can be interdigitated into the hydrophilic core of the bilayer membrane via the acyl chains of these compounds. Preferred hydrophilic targeting molecules include monoclonal antibodies, other immunoglobulins, lectins, and peptide hormones.

In addition to hydrophilic targeting molecules, it is also possible to use amphiphilic targeting molecules. Amphiphilic targeting molecules are normally not chemically coupled to the surfactant molecules but rather interact with the lipophilic or hydrophobic portions of the molecules constituting the bilayer lamellae of the lipid vesicles. Preferred amphiphilic targeting molecules are neutral glycolipids, galactocerebrosides (e.g., for hepatic galactosyl receptors), or charged glycolipids such as gangliosides.

The vesicles of the invention may further comprise sterols. Sterols useful in forming the lipid bilayers also include any sterol known in the art to be useful as modulators of lipid membranes. Suitable sterols include but are not limited to cholesterol, cholesterol derivatives, hydrocortisone, phytosterol, or mixtures thereof. In one embodiment, the sterol is phytosterol supplied from avocado oil unsaponifiables. The use of this sterol, in particular, to form lipid vesicles is described in issued U.S. Pat. No. 5,643,600, entitled "Lipid Vesicles Containing Avocado Oil Unsaponifiables", the contents of which are incorporated by reference herein.

In another embodiment, the invention pertains to a method for protecting the skin of a mammal. The method involves contacting the skin with a sprayable pharmaceutical petrolatum composition product which contains lipid vesicles encapsulating petrolatum dispersed in an external aqueous phase. The lipid vesicles are comprised of a primary wall forming material and a weighting agent. The primary wall forming material is a nonionic or a zwiterionic surfactant. The weighting agent is present in an amount sufficient such that the lipid vesicles have a density of about 0.95–1.0 g/mL.

Petrolatum filled vesicles may be formed using either the "hot loading" technique disclosed in U.S. Pat. No. 4,911,928, entitled "Paucilamellar Lipid Vesicles," or the "cold loading" technique described in U.S. Pat. No. 5,160,669, entitled, "Method of Making Oil Filled Paucilamellar Lipid Vesicles." The entire contents of both patents are incorporated herein by reference. In either case, a lipid phase is formed by blending a primary wall forming material and the weighting agent, along with any other materials to be incorporated into the lipid bilayers, to form a homogenous lipid phase. In the "hot loading" technique, the petrolatum is blended in the already formed lipid phase, forming a lipophilic phase.

Once a lipophilic phase is made, it is blended with an aqueous phase (e.g., water, saline, or any other aqueous solution which will be used to hydrate the lipids) under shear mixing conditions to form the vesicles. "Shear mixing conditions", as used herein, means a shear equivalent to a relative flow of 5–50 m/s through a 1 mm orifice. The paucilamellar lipid vesicles of the disclosure can be made by a variety of devices which provides sufficiently high shear for shear mixing. A device which is particularly useful for making the lipid vesicles of the present invention is described in U.S. Pat. No. 4,895,452, entitled "Method and apparatus for producing lipid vesicles."

In the "cold loading" technique, the lipid phase and the aqueous phase are blended under shear mixing conditions to form vesicles. Once the substantially aqueous filled lipid vesicles are formed, they are combined with the "cargo" material to be encapsulated, e.g., the petrolatum. Droplets of the water immiscible material enter the vesicles, presumably by a process resembling endocytosis. The vesicles are subsequently blended under low shear conditions, as described in U.S. Pat. No. 5,160,669.

The invention is further illustrated by the following Examples, which should not be construed as further limiting the subject invention. The contents of all references, issued patents, and published patent applications cited throughout this application including the background are hereby incorporated by reference.

EXEMPLIFICATION OF THE INVENTION

Example 1

Petrolatum Filled Vesicles

The following procedure was used to make vesicles of the invention. Tables 1–3 describe three different formulations of vesicles of the invention.

The lipid components of each vesicle preparation were weighed out into a stainless steel kettle and heated to 80° C. The materials were mixed together until a clear solution was obtained. Each clear solution was then cooled to 73–75° C.

The aqueous component of each vesicle preparations were weighed into a separate stainless steel kettle. An additional 2% of water was added to compensate for evaporation. Each solution was heated to 58–60° C.

Using a Novamix™ lipid vesicle machine (described in U.S. Pat. No. 4,895,452), the lipid and aqueous components of each vesicle preparation were separately mixed in a 1:1.70 ratio. Each sample was then stirred continuously and allowed to cool to room temperature before being stored. Microscopic analysis revealed small, regular, spherical vesicles for each of the sample formulations.

The vesicles of each sample were transferred directly from storage to a spraying apparatus, without being further diluted. Each of the samples was sprayed onto a black and white surface and analyzed. All of the samples were found to be satisfactory and commercially viable.

TABLE 1

| | Ingredients | % | Kg (for 100 Kg prep.) |
|---|---|---|---|
| LIPID PHASE | Glyceryl Distearate (Kessco, Stepan) | 3.60 | 3.60 |
| | Steareth-10 (Brij 76, ICI) | 2.00 | 2.00 |
| | Cholesterol USP (Maypro) | 1.00 | 1.00 |
| | Polysorbate 80 (Protameen) | 0.50 | 0.50 |
| | White Petrolatum USP (Penreco) | 30.00 | 30.00 |
| AQUEOUS PHASE | DI Water | 60.15 | 60.15 |
| | Urea USP | 2.00 | 2.00 |
| | Germaben II (ISP Van Dyk)* | 0.75 | 0.75 |

*propylene glycol, diazolidinyl urea, methyl paraben and propyl paraben.

TABLE 2

| | Ingredients | % | Kg (for 100 Kg prep.) |
|---|---|---|---|
| LIPID PHASE | Glyceryl Distearate (Kessco, Stepan) | 3.60 | 3.60 |
| | Steareth-10 (Brij 76, ICI) | 2.00 | 2.00 |
| | Cholesterol USP (Maypro) | 1.00 | 1.00 |
| | Polysorbate 80 (Protameen) | 0.50 | 0.50 |
| | White Petrolatum USP (Penreco) | 30.00 | 30.00 |
| AQUEOUS PHASE | DI Water | 63.95 | 63.95 |
| | Urea USP | 1.00 | 1.00 |
| | Germaben II-E* | 0.75 | 0.75 |

*propylene glycol, diazolidinyl urea, methyl paraben and propyl paraben.

TABLE 1

| | Ingredients | % | Kg (for 1500 Kg prep.) |
|---|---|---|---|
| LIPID PHASE | Glyceryl Distearate (Kessco, Stepan) | 3.60 | 54.00 |
| | Steareth-10 (Brij 76, ICI) | 2.00 | 2.00 |
| | Cholesterol USP (Maypro) | 1.00 | 15.00 |
| | Polysorbate 80 (Protameen) | 0.50 | 7.50 |
| | White Petrolatum USP (Penreco) | 30.00 | 450.00 |
| AQUEOUS PHASE | DI Water | 60.58 | 908.70 |
| | Sipon LSB (30% SLS) | 2.00 | 30.00 |
| | Methyl Paraben | 0.20 | 3.00 |
| | Propyl Paraben | 0.03 | 0.45 |
| | Sodium Chloride | 0.09 | 1.35 |

EQUIVALENTS

Those skilled in the art will recognize, or be able to ascertain using no more than routine experimentation, many equivalents to the specific embodiments and methods described herein. Such equivalents are intended to be encompassed by the scope of the claims.

What is claimed is:

1. A sprayable petrolatum product having paucilamellar lipid vesicles encapsulating petrolatum dispersed in an external aqueous phase, said paucilamellar lipid vesicles comprising a primary wall forming material, and a metal oxide weighting agent, said primary wall forming material being selected from the group consisting of nonionic and zwiterionic surfactants, and said weighting agent being present in an amount sufficient that said paucilamellar lipid vesicles have a density of about 0.95–1.0 g/ml.

2. The sprayable petrolatum composition of claim 1, wherein said primary wall forming material has the property that it will form a lipid vesicle in the absence of said weighting agent.

3. The sprayable petrolatum composition of claim 2 wherein said primary wall forming material is selected from the group consisting of polyoxyethylene glyceryl fatty acids, $C_{12}$–$C_{18}$ fatty alcohols, $C_{12}$–$C_{18}$ glycol monoesters, $C_{12}$–$C_{18}$ glyceryl mono- and diesters, polyoxyethylene fatty alcohols, betaines, sarcosinates, propylene glycerol stearate, sucrose distearate, glycerol bilaurate, glucosides, and mixtures thereof.

4. The sprayable petrolatum composition of claim 1, wherein said weighting agent is incorporated into the wall of said lipid vesicle.

5. The sprayable petrolatum composition of claim 1, wherein said weighting agent has a specific gravity greater than 1.0 g/ml.

6. The sprayable petrolatum composition of claim 1, wherein said weighting agent has a specific gravity between about 1.0 g/ml and 2.0 g/ml.

7. The sprayable petrolatum composition of claim 1, wherein said lipid vesicles further comprise a charge producing agent which minimizes flow of said external aqueous phase into said vesicles.

8. The sprayable petrolatum composition of claim 7, wherein said charge producing agent is selected from the group consisting of sodium lauryl sulfate, sodium laureth sulfate, sodium lactate, sodium pyrrolidone carboxylate, retinoic acid, aloe vera and urea.

9. The lipid vesicle of claim 1, wherein said petrolatum comprises at least about 20% by weight of said lipid vesicles.

10. The lipid vesicle of claim 9, wherein said petrolatum comprises at least about 30% by weight of said lipid vesicle.

11. A method for protecting the skin of a mammal by contacting said skin with a sprayable pharmaceutical petrolatum composition product having paucilamellar lipid vesicles encapsulating petrolatum dispersed in an external aqueous phase, said paucilamellar lipid vesicles comprising a primary wall forming material, and a metal oxide weighting agent, said primary wall forming material being selected from the group consisting of nonionic and zwiterionic surfactants, and said metal oxide weighting agent being present in an amount sufficient that said paucilamellar lipid vesicles have a density of about 0.95–1.0 g/ml.

12. The method of claim 11 wherein said primary wall forming material is selected from the group consisting polyoxyethylene glyceryl fatty acids, $C_{12}$–$C_{18}$ fatty alcohols, $C_{12}$–$C_{18}$ glycol monoesters, $C_{12}$–$C_{18}$ glyceryl mono-and diesters, polyoxyethylene fatty alcohols, betaines, sarcosinates, propylene glycerol stearate, sucrose bistearate, glycerol bilaurate, glucosides, and mixtures thereof.

13. The method of claim 11, wherein said weighting agent has a specific gravity greater than 1.0 g/ml.

14. The method of claim 13, wherein said weighting agent has a specific gravity between about 1.0 g/ml and 2.0 g/ml.

15. The method of claim 11, wherein said lipid vesicles further comprise a charge producing agent which minimizes flow of said external liquid phase into said vesicles.

16. The method of claim 15, wherein said charge producing agent is selected from the group consisting of sodium lauryl sulfate, sodium laureth sulfate, sodium lactate, sodium pyrrolidone carboxylate, aloe vera, retinoic acid and urea.

* * * * *